Figure 9:
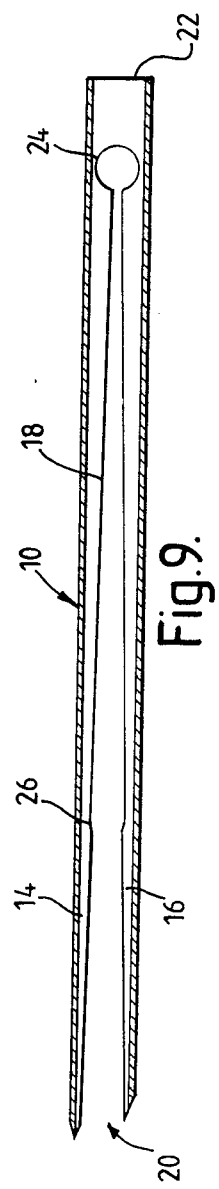

United States Patent [19]

Jackson et al.

[11] Patent Number: 4,716,901
[45] Date of Patent: Jan. 5, 1988

[54] SURGICAL APPLIANCE FOR FORMING AN OPENING THROUGH THE SKIN

[75] Inventors: Joseph F. Jackson, Halifax; Steven S. Gill, Knebworth, both of England

[73] Assignee: Pratt Burnerd International Limited, United Kingdom; a part interest

[21] Appl. No.: 779,810

[22] Filed: Sep. 25, 1985

[30] Foreign Application Priority Data

Sep. 27, 1984 [GB] United Kingdom ............... 8424436

[51] Int. Cl.⁴ ............................................. A61M 29/00
[52] U.S. Cl. ............................. 128/343; 128/200.26; 128/305.3; 604/106; 604/160; 604/272
[58] Field of Search ................. 128/341, 343, 200.26, 128/305.3, 335; 604/106, 158, 160, 272

[56] References Cited

U.S. PATENT DOCUMENTS

| | | | |
|---|---|---|---|
| 3,662,754 | 5/1972 | Halloran | 604/272 |
| 3,688,773 | 9/1972 | Weiss | 128/305.3 |
| 3,788,318 | 1/1974 | Kim et al. | 128/343 X |
| 3,789,852 | 2/1974 | Kim et al. | 128/347 |
| 3,877,429 | 4/1975 | Rasumoff | 604/158 |

FOREIGN PATENT DOCUMENTS

| | | | |
|---|---|---|---|
| 2203648 | 5/1974 | France | 128/343 |
| 632812 | 12/1947 | United Kingdom | 128/343 |

Primary Examiner—William R. Cline
Assistant Examiner—Peggy A. Neils
Attorney, Agent, or Firm—Richard E. Jenkins

[57] ABSTRACT

The invention relates to a surgical appliance for forming an opening through the skin of a patient and for distending the opening so formed. The appliance takes the form of a trocar which may comprise two separate components or two component portions formed by openings in a tube extending partially along the tube from the distal end. In either case, the components or component portions are preloaded towards a closed condition, but can be expanded into an open condition, for example by forcing a tubular expander into the trocar from the proximal end. The preloading of the trocar may be by a resilient sleeve surrounding the components or by a "set" introduced into the material forming the components. A cutting edge may be formed across substantially the full width of the distal end of the trocar and it is preferred that in the open condition, there is a no significant increase in the cross-section of the trocar towards the distal end.

11 Claims, 13 Drawing Figures

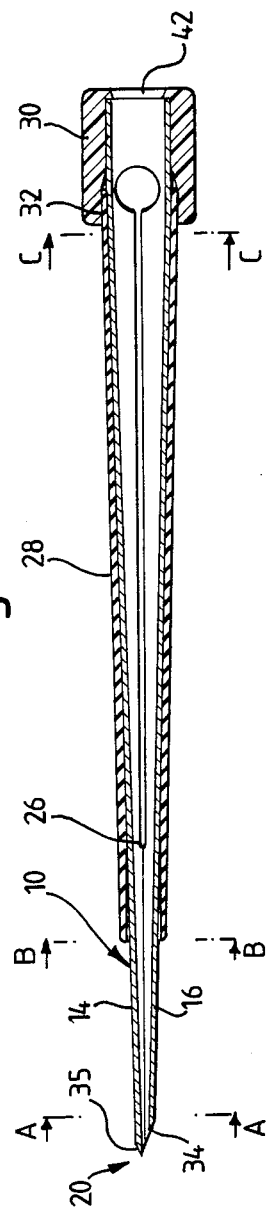
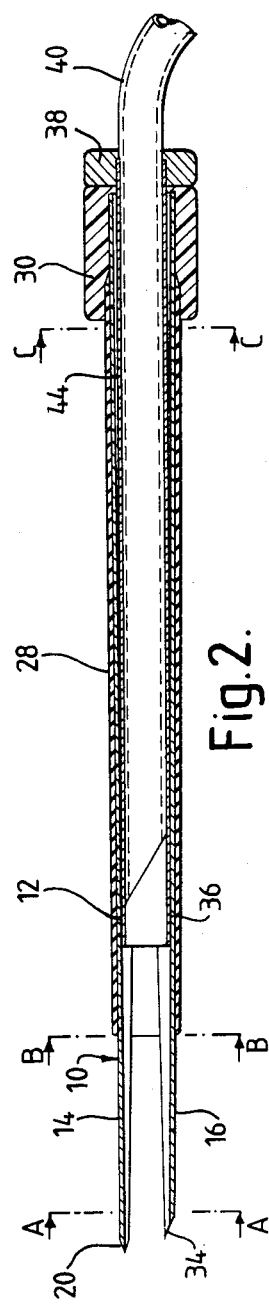

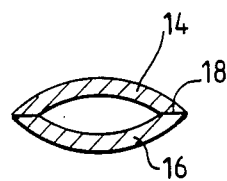
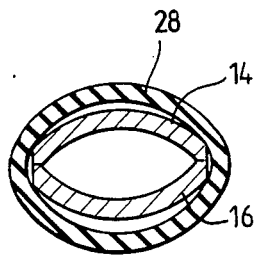
Fig.3.  Fig.4.
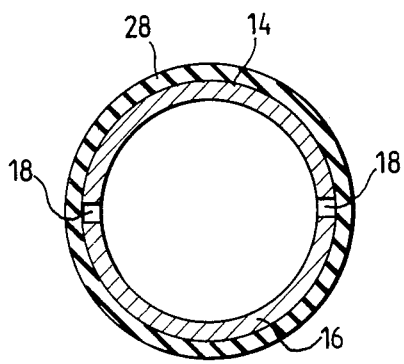
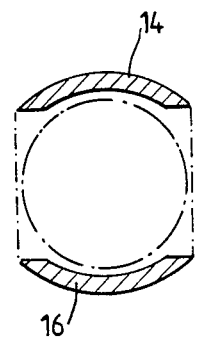
Fig.5.  Fig.6.
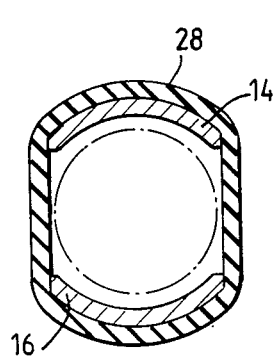
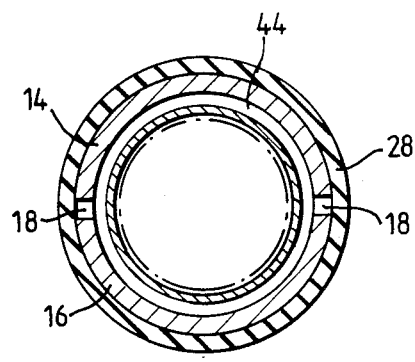
Fig.7.  Fig.8.

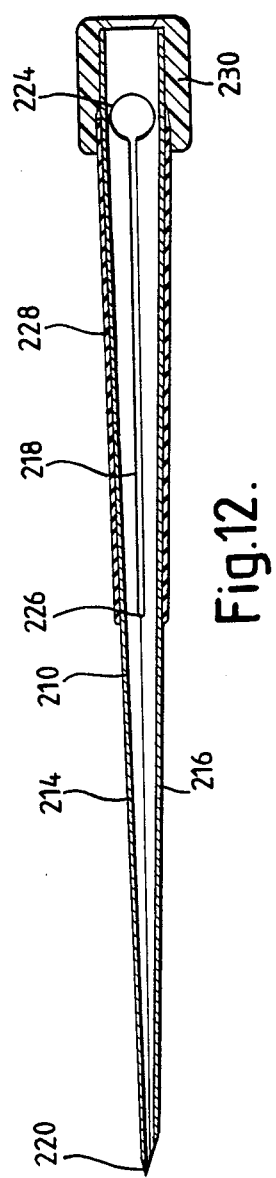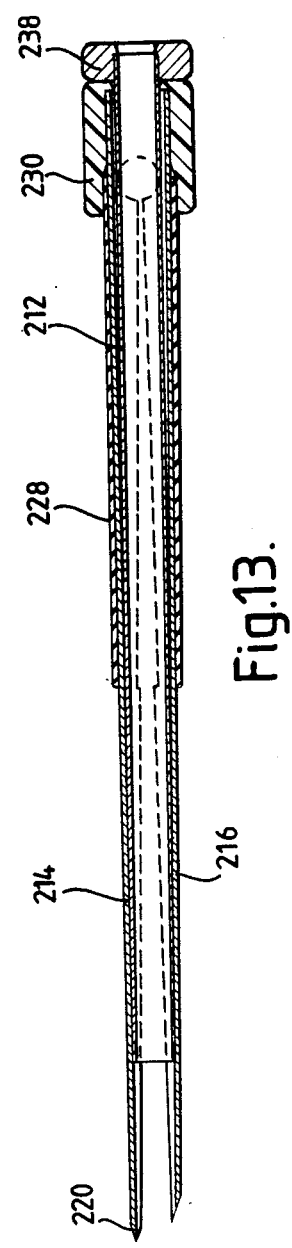

SURGICAL APPLIANCE FOR FORMING AN OPENING THROUGH THE SKIN

The present invention relates to a surgical appliance and to a method for forming an opening through the skin of a patient or animal. The invention is applicable to the treatment of humans and will be so described hereinafter, but it should be understood, that, with approprite modifications, it could also be applied in veterinary practice. Whilst the method and apparatus can be used in a variety of surgical operations, it is particularly useful for introducing drainage tubing, scopes, instruments, wire or other surgical and exploratory apparatus into cavities, and it may be used for instance for introducing drainage tubing into the thoracic cavity, or for radiological intervention.

Taking the insertion of a thoracic drainage as an example, the current method of drain insertion requires initially the cleaning of the skin at the site of insertion under sterile conditions. Local anaesthetic is infiltrated into the intercostal space, traversing the upper border of a rib. A 2 centimeters long incision is made at the site, and 2 sutures are inserted, one for securing the drain in place, and a second, more loosely applied, purse string suture for use in subsequent closure of the incision when the drain is removed. Dissection is made through the connective tissue and intercostal muscle into the pleura. The chest drain can be inserted by means of an Argyle-type assembly, in which the drain is placed over a long trocar and forced through the incision into the pleural space, and the central trocar then removed. Alternatively, it can be introduced using the Tudor-Edwards assembly in which a trocar with surrounding cannula are pushed through the incision into the pleural space, the trocar withdrawn and the drainage tube is then passed through the cannula and the cannula removed over the drain leaving the drain alone in-situ. Both the Argyle trochar, and the Tudor-Edwards trochar and the cannula can be made to various sizes to accept standard catheters, such as 24F and 28F of sizes 8 millimeters and 9.3 millimeters in diameter respectively. Once the drain is in-situ it is secured with a suture and connected to the underwater arm of an underwater seal drain.

There have been proposals for expansible trocars which can be expanded after insertion through the skin of a patient to allow a drain tube or breathing tube to be threaded through the expanded trocar. An expansible device for use in tracheostomy is described in the specification of United Kingdom Pat. No. 1 401 026. It comprises a housing with a sharpened distal end portion which is intended to penetrate the skin and the trachea of a patient. The housing is made in two parts, and the distal end of the housing is adapted to be expanded by moving the two parts away from each other by the insertion of a tube. The construction is such that the expanded distal end portion of the device is flared outwardly towards its end (i.e. it is wider inside the trachea than at the position where it passes through the wall of the trachea). The expanded device seals quite firmly to the wall of the trachea as is required for a successful tracheostomy. The device described in Pat. No. 1 401 026 is quite complicated, and therefore expensive to use. For that reason alone, it cannot be regarded as a single use item, but must be resterilised after use for subsequent reuse. Moreover, the method of expansion requires the application of considerable force which is not conducive to accurate control over the insertion technique.

According to one aspect of the invention a surgical appliance for forming an opening through the skin of a patient or an animal comprises a trocar having a distal end which is intended to penetrate the skin; the trocar comprising a generally parallel-sided tube divided through part only of its length from the distal end, by two cut-away parts of the wall of the tube into two component parts or portions, which by virtue of the cut-away openings in the wall of the tube are adapted to move relatively to each other between a closed condition and an open condition, the two components being preloaded into the closed condition, in which they converge towards the distal end as permitted by the openings in the wall of the tube, and an expander which can be inserted into the trocar from the proximal end towards the distal end, and which when so inserted causes movement of the trocar components against the preloading to the open condition.

The trocar is inserted through the skin of the patient with its two components in the closed condition, which facilitates entry of the trocar through the incision. Once it has been inserted, the trocar components are opened by operation of the expander, and this distends the skin around the incision to form an opening of a required shape and size which will be determined by the shape and size of the trocar when its components are in the open condition. Thus, the reference to forming an opening as used herein, includes the distending of the incision to the required shape and dimensions.

One method of preloading the trocar components is the provision of a resilient ring or sleeve fitted around the two trocar components, the bore of the ring or sleeve in its free condition, being such that it applies an inward compressive force to the components. Another method of preloading is to deform the trocar components inwardly (i.e. towards each other) beyond the elastic limit of the material from which the tube is made, so that the components adopt a "set" in the closed condition and the preloading is then provided by that permanent "set". A combination of these two methods may be used.

Preferably each of the cut-away openings tapers along the length of the tube, being widest at the distal end. This arrangement permits the trocar components to adopt an inwardly tapering attitude towards the distal end when in the closed condition. It is further preferred that the cut-away openings extend over most of the length of the tube.

It is still further preferred that the design of the trocar is such that when it is in the open condition there is no substantial increase in the cross-section of the trocar towards the distal end. This ensures that the trocar can be withdrawn from the hole through the skin without any significant distending or tearing of the skin during the withdrawal.

Preferably the arrangement is such that the trocar does not increase substantially in any cross-sectional dimension towards its distal end at any position from its closed to open conditions. It is further preferred that the trocar tapers towards its distal end in the closed condition. In fact, the trocar may taper towards its distal end somewhat even in the open condition, though it may be only slightly tapered or substantially parallel-sided in the open condition.

According to another preferred feature of this aspect of the invention the distal end of the trocar is formed with one or more cutting edges adapted to make an incision in the skin as that end of the trocar is forced through the skin, the cutting edge or edges extending across substantially the full width of the distal end of the trocar in the closed condition, so that the total peripheral length of the incision is approximately twice the width of the distal end of the trocar. This feature enables the appliance to form its own incision as the trocar is forced through the skin. Moreover, if, for example, the peripheral length of the hole in the skin when distended to allow the trocar to pass is say three times the width of the distal end of the trocar, then the stretching of the skin around the hole during insertion is 50% which can be achieved in most cases without tearing.

According to a second aspect of the invention a surgical appliance for forming an opening through the skin of a patient or an animal comprises a trocar having a distal end which is intended to penetrate the skin; the trocar comprising two components with one or more cutting edges adapted to make an incision in the skin as that end of the trocar is forced through the skin, the cutting edge or edges extending across substantially the full width of the distal end of the trocar; the said two components being adapted to move relatively to each other between a closed condition and an open condition; the arrangement being such that in the open condition, there is no substantial increase in the cross-section of the trocar towards its distal end, and the components being preloaded towards the closed condition, and an expander which can be inserted into the trocar from the proximal end towards the distal end, and which when so inserted causes movement of the trocar components to the open condition.

According to another preferred feature of the second aspect of the invention, the arrangement is such that there is a channel through the trocar components when they are in the open condition. (It will be appreciated that such a channel is automatically provided in an appliance in accordance with the first aspect of the invention, by virtue of the tubular form of the trocar.) The trocar components in this second aspect of the invention may be completely separate parts, but in the preferred construction they are portions of a single element, partially divided from each other by a slit or slits.

The expander which may be used with either the first or second aspects of the invention, preferably comprises a rigid tube, the outside diameter of which is equal to the spacing between the trocar components when in the open condition, so that when the tube is inserted through the proximal end of the trocar, it engages with the insides of the trocar components and forces them apart. The expander tube itself provides a central opening through itself, which when the trocar components are opened, is in continuation of the central channel through those components, whereby it is possible to pass a tube through the entire appliance when the trocar components are open.

According to another preferred feature of the invention, the arrangement of the trocar components is such that a longitudinal movement of at least 2 centimeters of the expander is required to move the components from the closed condition to the open condition. This ensures that there is a steady opening of the trocar under the action of the expander, rather than a sudden motion, which would require the exertion of a relatively large force to the expander. Preferably the insides of the trocar components taper uniformly, so that there is a uniform expansion during the said longitudinal motion of the expander. In the preferred embodiment, a longitudinal motion of about 5 centimeters is employed for the total opening of the trocar.

It is a significant feature of the second aspect and the preferred form of the first aspect of the invention that there is no substantial increase in the cross-section of the trocar towards the distal end when it is in the open condition, because this means that it is possible to withdraw the trocar and the expander, without having to close the trocar (which will be impossible if a tube of maximum size is passed through it) and without tearing the skin of the patient.

Another advantage of the present invention is that the construction of the appliance is very simple, so that it can be made cheaply. Indeed, it is possible to regard the appliance as a single use item, i.e. it can be discarded after a single use, thus avoiding the necessity for resterilisation and obviating the danger of cross infection.

According to another preferred feature of the second aspect of the invention, each trocar component has a blade-like configuration, the blades being bowed outwardly as seen in lateral cross-section, so that in their closed condition, the components contact each other only along the longitudinal edges, and in the open position, they approximate in cross-section to parts of an annulus the internal diameter of which is large enough for the passage of a drain tube. Again, this is a feature which is automatically provided by the first aspect of the invention.

According to yet another preferred feature which is applicable to both the first and second aspects of the invention a distendable tube is fitted around the parts of the trocar components which will not penetrate the skin in use, to prevent ingress of air through the openings formed between the components when the latter are moved into the open condition.

Figure 10:
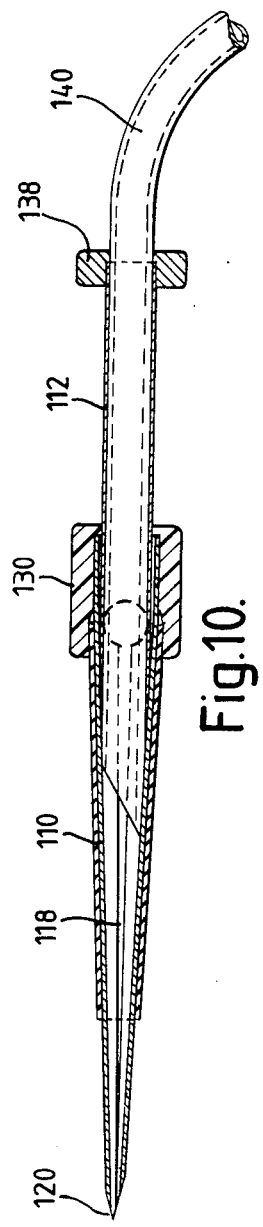

Three constructions of surgical appliances each in accordance with both aspects of the invention, will now be described by way of examples only, with reference to the accompanying drawings, in which:

FIG. 1 is a longitudinal section through a thoracic drain introducer shown in the closed condition, FIG. 2 is a longitudinal section of the thoracic drain introducer shown in FIG. 1 in an open condition, FIG. 3 is a cross-section on the line A—A in FIG. 1, FIG. 4 is a cross-section on the line B—B in FIG. 1, FIG. 5 is a cross-section on the line C—C in FIG. 1, FIG. 6 is a cross-section on the line A—A in FIG. 2, FIG. 7 is a cross-section on the line B—B in FIG. 2, FIG. 8 is a cross-section on the line C—C in FIG. 2, FIG. 9 is a longitudinal section through a trocar blade forming part of the appliance shown in FIG. 1 but in the open condition, FIG. 10 is a longitudinal section through an alternative form of thoracic drain introducer shown in a closed condition.

Figure 11:
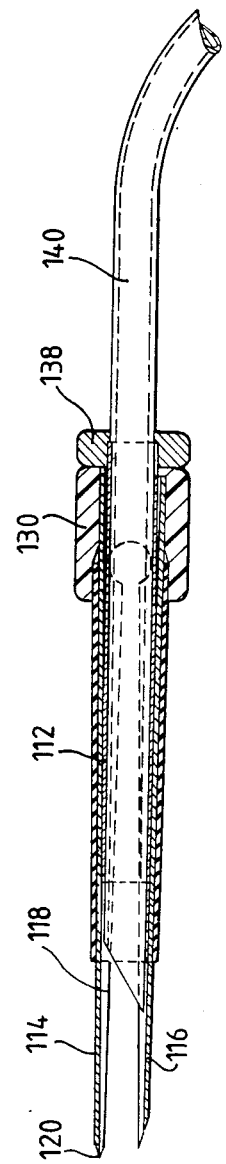

FIG. 11 is a longitudinal section through the thoracic drain introducer shown in FIG. 10, in the open condition, FIG. 12 is a longitudinal section through a radiological intervention introducer shown in the closed condition, and FIG. 13 is a longitudinal section through the radiological intervention introducer of FIG. 12, shown in the open condition.

Referring to the thoracic drain introducer which is illustrated in FIGS. 1 to 9, basically this comprises a trocar 10 and an expander 12. The trocar 10 is generally tubular, and in fact is made from a stainless steel or plastics tube. As is clear from FIGS. 1, 2 and 9, the trocar is of appreciable length, and the bore of the tube is larger in diameter, than the outside diameter of the thoracic drain tube which is to be used with it. For instance, if the introducer is to be used with a size 28F standard catheter, of 9.3 millimeters outside diameter, the bore of the tube from which the trocar is made, may be 12.4 millimeters. The overall length of the trocar may be in the order of 240 millimeters.

As is apparent from FIG. 9, the tube from which the trocar is made, is divided into two components 14 and 16 by diametrically opposed longitudinally extending cut-away openings 18. Each of the openings 18 extends through most of the length of the tube from the distal end 20, but near to the proximal end 22, each opening 18 terminates in a stress-relieving circular hole 24 and beyond that, the tube is not cut away. It is to be noted that each opening 18 also tapers inwardly from the distal to the proximal end of the tube, so that where it joins the hole 24, it is quite narrow, whereas at the distal end 20, it is relatively wide. There is also a small step in the width of the opening 18, about a third of the distance from the distal end 20 to the hole 24. The shape of the opening 18 results in the formation of the two trocar components 14 and 16, which at the distal end subtend only small angles around the longitudinal axis of the trocar, whereas at the proximal end, adjacent to the hole 24, they together subtend almost the entire 360° around the longitudinal axis. However, each component 14 and 16 throughout its length is of arcuate cross-section, as indicated in FIGS. 3, 4 and 5.

The proximal end of the trocar tube is bonded into a short cylindrical plastics holders 30, which provides a high degree of rigidity to that end of the tube, leaving the major part of the length of the trocar tube extending cantilever fashion from the body. Further, the body 30 provides a hand grip for the appliance. A long rubber sleeve 28 is fitted around the major part of the length of the trocar tube, and the proximal end of this sleeve is received in a counter bore 32 in the body 30. As illustrated in FIGS. 1 and 2, the sleeve 28 extends forwardly of the step 26 in the openings 18, but terminates an appreciable distance short of the distal end 20 of the appliance. The sleeve 28 is, in the free condition, of considerably smaller diameter than the outside diameter of the tube from which the trocar is made, so that the sleeve exercises an inward constraining force on the trocar components 14 and 16. As a result, the parts of the components 14 and 16 forward of the step 26 in the openings 18 are pressed into engagement with each other, as clearly shown in FIGS. 1 and 3. Thus the rubber sleeve provides a radial inward constraining force on the components 14 and 16 and urges them into the closed condition. In that condition, the forward end of the sleeve 28 adopts an elliptical form as illustrated in FIG. 4. Adjacent to the body 30, the sleeve 28 is fully distended, to accommodate the larger ends of the components 14 and 16.

This produces the closed condition of the appliance, illustrated in FIG. 1 wherein the distal end parts of the components 14 and 16 close onto each other. The distal extremities of the components 14 and 16 are backed-off, as indiciated at 34 and 35 so that in the fully closed condition of the trocar, they provided (i) a point for piercing the skin and (ii) two sharpened converging edges for cutting the skin as the distal end 20 is forced through the skin. The cutting edges together extend across the full width of the components 14 and 16; this ensures that the incision made by the cutting edges in the skin of the patient is wide enough to permit the distal end portion of the trocar to pass through the skin with substantially no distending of the skin around the incision.

In the closed condition, the trocar tapers throughout its effective length between the body 30 and the distal end 20, so that its cross-sectional area is diminishing throughout the length between the body 30 and the pointed end 20. The diminution of the vertical cross-section as shown in FIG. 1, is greater than the diminution in the horizonal cross-section, but there is no cross-sectional dimension of the trocar which increases to any significant extent from the proximal to the distal end in the closed condition. This assists in the insertion of the trocar through an incision made in the skin of a patient by the cutting edges, because as the tapering trocar is passed through the incision, the incision is gradually distended by the increasing cross-sectional area of the trocar.

The expander 12 essentially comprises a thin metal or plastics tube 36 somewhat shorter than the trocar, and bonded at one end into the bore of a ring 38 (see FIG. 2). The bore of the expander tube 38 is just large enough to allow a thoracic drain tube 40 of the size with which the appliance is intended to be used, to slide easily therethrough. The expander tube 36 has to remain substantially rigid, but given that requirement, it is otherwise made as thin walled as possible. In a typical example, where the expander tube 36 is adapted to permit a 9.3 millimeters diameter drain tube to slide through it, the outside diameter of the expander may be 11 millimeters (i.e. the wall thickness is about 0.75 millimeters).

In use, the distal end of the expander tube 36 is introduced into the proximal end of the trocar, passing through an inlet hole 42 in the body 30, and then through the bore of the trocar tube. Once the forward end of the expander tube reaches the position at which the trocar components 14 and 16 begin to taper towards each other (i.e. in front of the hole 24) the advancing motion of the expander tube 36 causes the trocar components 14 and 16 to be progressively forced apart, against the constraining action of the rubber sleeve 28. Eventually, the fully opened condition is arrived at as illustrated in FIG. 2. Since the trocar components taper evenly towards each other from the proximal to the distal end, an appreciable longitudinal motion of the expander tube 12 is required in order to open the trocar fully. This is advantageous, because it ensures that a steady force is required to be applied to the expander tube, in opening the trocar components. In practice, a movement of about 5 centimeters is required to carry out the opening motion where the trocar tube is about 240 millimeters long.

In the fully opened condition, the ring 38 engages with the rear end of the body 30, thus limiting the motion of the expander tube into the trocar, and the components 14 and 16 are then only slightly tapered towards each other towards the distal end 20. The existence of the taper can be noted by reference to the narrow annular gap 44 between the inside of the trocar components and the outside of the expander sleeve at the proximal end of the trocar. The condition of the trocar components 14 and 16 in the open condition is well illustrated in FIGS. 6, 7 and 8, as is the existence of the gap 44 at the proximal end of the trocar.

The manner in which the thoracic drain introducer shown in FIGS. 1 to 9 is used to carry out a drain tube introduction, will now be described to assist in understanding the invention. Before using the appliance on a patient, the thoracic drain tube 40 is introduced through the proximal end of the expander 12. The forward end of the tube 40 is cut off obliquely as illustrated in FIG. 2. Prior to insertion of the drain, the site of insertion is cleaned under sterile conditions and local anaesthetic is injected into the intercostal space. The expander 12 with the drain tube (which is plugged at the other end) fitted into it, is pushed into the trocar as just described. Then the distal end 20 of the trocar, still in the closed condition illustrated in FIG. 1, is inserted through the skin and intercostal muscles into the thoracic cavity. The sharpened end of the trocar and the cutting edges form an incision through the skin to facilitate entry of the remainder of the trocar. However, entry of the trocar is also facilitated, because the thickness of the distal end is quite small in comparison to currently available trocars as used for thoracic drain insertion. Moreover, the gradual taper of the trocar components 14 and 16 in the closed condition produces a gradual distending of the opening through the skin, without a tearing action.

The trocar is prevented from being inserted beyond the desirable length by engagement of the end of the rubber sleeve 28 with the skin. The person carrying out the operation will hold the trocar by the body 30, and push the expander tube, by pressing on the ring 38, through the trocar. As the rigid expander tube passes forwardly through the trocar components 14 and 16, it forces them apart, and the skin and intercostal muscles are stretched, creating a channel into the intercostal space. Eventually, the fully opened condition is arrived at, where the ring 38 abuts against the body 30.

It is a significant feature of the invention that the insertion and expansion can be achieved with little or no tearing of the skin. To take a specific example; if the cutting edges make an incision approximately 1 centimeter wide, the periphery of the incision is 2 centimeters. The hole formed by expansion of the trocar may then have a periphery of about 3 centimeters, i.e. there is a 50% distending of the skin around the hole, and this may well be achieved without tearing.

The drain tube 40 can then be slid easily through the expander 12, and through the opened forward portions of the components 14 and 16 into the pleural space.

Finally, the trocar 10 is withdrawn, by gripping the body 30, and pulling it outwardly. Because the body 30 engages with the ring 38, both the trocar 10 and the expander 12 move together in this extraction direction, and slide over the thoracic drain tube 40. Since the forward portions 14 and 16 of the trocar are not splayed apart (and indeed are still slightly tapered towards each other) removal of the trocar from the skin of the patient is accomplished without tearing action. The skin and the intercostal muscles which have been stretched on the opening of the trocar then contract on to the drain tube 40, gripping it firmly. On the expansion of the trocar, the peripheral length of the opening in the skin may have been overstretched relatively to the outside diameter of the drain tube by say 25%, but this amount of overstretch is acceptable and will be taken up by contraction of the opening on withdrawal of the appliance. After the trocar has been completely removed from the drain tube 40, the exposed part of the drain may then be further secured to the chest wall with adhesive tape, or other known means, and the drain connected to the underwater arm of an underwater seal drain.

In the foregoing description, the function of the rubber sleeve 28 has been described as (i) providing the preloading force constraining the components 14 and 16 into the closed condition, and (ii) limiting the insertion of the trocar into the patient. The sleeve 28 has another function in that it covers the openings 18 in the part of the trocar which does not enter the patient. This prevents the ingress of air through those openings and then through the tube passage through the trocar when the latter is being inserted. The sealing against ingress of air is essential in some instances and is further ensured by the distal end of the sleeve 28 pressing against the skin around the hole formed by the trocar during insertion and withdrawal of the appliance. If sealing against the ingress of air is not vital, then the long sleeve 28 may be replaced by a short rubber or plastics ring, which is required only to apply the radial inward force and to provide a location stop to prevent over insertion of the trocar.

However, as an alternative to the use of a resilient sleeve or ring, the components 14 and 16 may be pressed into the closed condition during manufacture and given a permanent "set" into that condition. It is still possible to expand the trocar using the expander 12, but the constraining force is provided by the components 14 and 16 themselves and expansion is permitted by the inherent resilience of those components. It will be appreciated that even with this construction, the rubber sleeve 28 may still be required to seal against air ingress. Also, it is possible to use a combination of presetting the components into or towards the closed condition and a constraining ring or sleeve.

It is also possible to flatten the distal extremities of the components 14 and 16, so that they are completely closed on to each other, i.e. there is no central opening between them as indicated in FIG. 3. This further assists both in the provision of the point and cutting edges and in the insertion of the trocar.

Turning now to FIGS. 10 and 11, there is illustrated a thoracic drain introducer, which in principle is similar to that described with reference to FIGS. 1 to 9, the main difference being that the trocar is much shorter, since for some operations, it is preferred that the trocar should be as short as possible.

Again, the appliance has a tubular trocar 110, and a rigid tubular expander 112. The tubular trocar 110 is divided by diametrically opposed openings 118 into two trocar components 114 and 116 having a sharpened distal end 120. Moreover, the proximal end of the trocar tube is received in a body 130 and the rigid tubular expander 112 is received in a ring 138. A thoracic drain tube 140 is also illustrated.

It is unnecessary to described the appliance illustrated in FIGS. 10 and 11 in greater detail, because it will be apparent, that the construction and function is very similar to that of the appliance illustrated in FIGS. 1 to 9.

In FIGS. 12 and 13 there is illustrated a radiological intervention introducer, which again is quite similar in construction and use to the appliance shown in FIGS. 1 to 9, although in this instance, the bore of the expander can be smaller, because it is only intended to introduce appliances such as wires and cables rather than drain tubes through the skin of the patient.

Again, there is a tubular trocar 210 and a rigid tubular expander 212. The tubular trocar 210 tapers rather more sharply than the trocar 10 illustrated in FIG. 1, but it has diametrically opposed openings 218 dividing it into trocar components 214 and 216, which extend almost through the whole length of the trocar, from a distal end 220, which is sharpened and formed with cutting edges, to a hole 224 formed at the end of each opening 218 near to the proximal end of the trocar tube. Moreover, as in previous constructions, the trocar tube is received in a body 230 which also provides a hand grip. It will be noted that the step 226 in the opening 218 is about half way along the length of the trocar tube from the distal end 220 to the body 230, that is the forwardly extending parts of the components 214 and 216 which engage with each other (as illustrated in FIG. 3) form a greater proportion of the length of the trocar than in the construction illustrated in FIG. 1.

There is also a rubber sleeve 228 surrounding the trocar components on the proximal side of the step 226, and performing the functions of the sleeve 28 previously described.

The tubular expander 212 extends from a ring 238, and can be pushed into the trocar through the body 230, for the purpose of expanding the components 214 and 216 against the resilient action of the sleeve 228. It will be noted from FIG. 13 however, that in the fully open condition, where the ring 238 abuts against the body 230, the distal end of the expander tube 212 is well forward of the forward termination of the sleeve 228. Indeed, the expander tube can be made long enough to extend to the distal end of the trocar to support the components 14 and 16 in the open condition. This forward portion of the expander tube can provide a journal bearing for a rotating tool in some operations.

The radiological intervention introducer illustrated in FIGS. 12 and 13 is used in a similar manner to that described with reference to FIGS. 1 to 9, excepting that after the expander 212 has been fully inserted, in order to open up the incision formed through the skin of the patient, then instead of passing a drain tube through the bore of the expander, an operating tool, a wire, optical fibre or the like is passed through that bore into the required location within the patient.

In some instances, a guide wire will already have been passed through the skin of the patient into a desired location in an organ on which an operation is to be performed. The appliance illustrated in FIGS. 12 and 13 is then threaded over this guide wire and can be used as previously described, excepting that the location of the opening formed by the trocar is determined by the guide wire and the trocar, and any tube passed through the trocar, follows the guide wire to the organ on which the operation is being performed.

For some operations, it will be possible to leave the introducer in-situ, until the operation has been completed. For other operations however, the introducer is withdrawn by pulling it away from the patient, thus extracting the trocar components 214 and 216 from the distended incision. The walls of the incision then close tightly around whatever has been introduced through the bore of the expander.

The extreme simplicity of construction of the device in accordance with the invention, means that it can be produced relatively cheaply. Consequently, after a single use, the appliance can be discarded, rendering it a disposable item. It will be appreciated, that this eliminates the necessity for resterilisation of the appliance, and also ensures that there cannot be any cross-infection arising out of use of the appliance.

It will also be appreciated, that the construction may be varied from that which is illustrated in the drawings, without departing from the scope of the invention. It will further be appreciated that any of the features described with reference to any one of the three preferred embodiments described above could be employed on either of the other two embodiments.

We claim:

1. A surgical appliance for forming an opening through the skin comprising: a trocar having a distal end which is adapted to penetrate the skin, and a proximal end; said trocar comprising a generally parallel-sided tube divided through only part of its length from said distal end, by two cut-away parts of the wall of the tube, into two component portions, which, by virtue of said cut-away openings in the wall of said tube, are able to move relatively to each other between a closed condition wherein said two component portions converge towards said distal end and an open condition; preloading urging said two component portions towards said closed condition; an expander which can be inserted into said trocar from said proximal end, and which when so inserted and traversed towards said distal end, causes a progressive movement of said trocar component portions against said preloading into said open condition wherein they permit free passage of said expander therethrough, and a distendable tube fitted around the parts of said trocar components which do not penetrate the skin in use, said distendable tube having an internal diameter in the free condition such that it provides at least part of said resilient loading, said tube further preventing ingress of air through the openings formed between said trocar components in the open condition.

2. A surgical appliance according to claim 1, wherein part of said preloading is provided by deforming said trocar component portions inwardly towards each other beyond the elastic limit of the material from which said tube is made, so that said component portions adopt a "set" in said closed condition which "set" itself provides said preloading.

3. A surgical appliance according to claim 1, wherein said distal end of said trocar is formed with at least one cutting edge for making an incision in the skin as that end of said trocar is forced through the skin, said at least one cutting edge extending across substantially the full width of said trocar at said distal end in said closed condition, whereby the total peripheral length of an incision made by insertion of said trocar is approximately twice the width of said distal end.

4. A surgical appliance for forming an opening through the skin comprising: a trocar having a distal end which is adapted to penetrate the skin, and a proximal end; said trocar comprising two components formed with at least one cutting edge which is adapted to make an incision in the skin when said distal end of the trocar is forced through the skin; said at least one cutting edge extending across substantially the full width of said distal end; means whereby said two components are adapted to move relatively to each other, between a closed condition and an open condition; the arrangement of said components being such that in said open condition, there is no significant increase in the cross section of said trocar towards said distal end; a distendable tube fitted around the parts of said trocar components which do not penetrate the skin in use and having an internal diameter such that it provides at least part of preloading urging said two components towards said closed condition; and an expander which can be inserted into said trocar from said proximal end towards said distal end, said insertion of said expander causing movement of said trocar components to said open condition.

5. A surgical appliance according to claim 4, wherein said trocar components define a channel through the trocar from the proximal to the distal end thereof when said components are in said open condition.

6. A surgical appliance according to claim 4, wherein said trocar components are portions of a single element, partially divided from each other by at least one slit in the element.

7. A surgical appliance as claimed in claim 1, wherein said expander comprises a rigid tube, having an outside diameter equal to the spacing between said trocar component portions when said component portions are in said open condition, whereby when said rigid tube is inserted through said proximal end of said trocar, it engages with the insides of said component portions and forces them apart.

8. A surgical appliance according to claim 4, wherein said expander comprises a rigid tube, having and outside diameter equal to the spacing between said trocar components when said components are in said open condition, whereby, when said rigid tube is inserted through said proximal end of said trocar, it engages with the insides of said components and forces them apart.

9. A surgical appliance according to claim 4, wherein each trocar component has a blade-like configuration, said blades being bowed outwardly as seen in lateral cross-section, so that in their closed condition, said components contact each other only along their longitudinal edges, and in the open condition said components approximate in cross-section to parts of an annulus, the internal diameter of which is large enough for the passage of a drain tube.

10. A surgical appliance for forming an opening through the skin comprising: a trocar having a distal end which is intended to penetrate the skin, and a proximal end; said trocar comprising a generally parallel-sided tube, divided through only part of its length from said distal end by two cut-away parts of the wall of the tube, into two component portions, which, by virtue of said cut-away openings in the wall of said tube, are able to move relatively to each other between a closed condition and an open condition; the arrangement of said component portions being such that in said open condition, there is no significant increase in the cross section of said trocar towards said distal end; said component portions being formed with at least one cutting edge which is adapted to make an incision in the skin when said distal end of the trocar is forced through the skin; said at least one cutting edge extending across substantially the full width of said distal end; a distendable tube fitted around parts of said trocar components which do not penetrate the skin in use and having an internal diameter such that it provides at least part of preloading urging said two component portions towards said closed condition, wherein said component portions converge towards said distal end.

11. A surgical appliance according to claim 1, wherein said trocar components are so constructed that movement of at least two centimeters of the expander in engagement with said trocar components is required to move said components into said open condition, and in said open condition, the cross section of said trocar at said distal end is no greater than at said proximal end whereby the movement of the trocar components into the open condition may be used to gradually distend an incision through which the trocar extends, but the trocar can be withdrawn from the distended incision without any significant distending or tearing of the skin during the withdrawal.

* * * * *